United States Patent
Minato et al.

(10) Patent No.: US 9,269,134 B2
(45) Date of Patent: Feb. 23, 2016

(54) INSPECTION AREA SETTING METHOD FOR IMAGE INSPECTING DEVICE

(75) Inventors: Yoshihisa Minato, Kyoto (JP); Yukiko Yanagawa, Nara (JP)

(73) Assignee: OMRON Corporation, Kyoto (JP)

(*) Notice: Subject to any disclaimer, the term of this patent is extended or adjusted under 35 U.S.C. 154(b) by 0 days.

(21) Appl. No.: 14/363,340

(22) PCT Filed: Aug. 29, 2012

(86) PCT No.: PCT/JP2012/071758
§ 371 (c)(1),
(2), (4) Date: Jul. 1, 2014

(87) PCT Pub. No.: WO2013/103032
PCT Pub. Date: Jul. 11, 2013

(65) Prior Publication Data
US 2014/0314302 A1    Oct. 23, 2014

(30) Foreign Application Priority Data
Jan. 5, 2012  (JP) .................................. 2012-000588

(51) Int. Cl.
*G06K 9/00* (2006.01)
*G06T 7/00* (2006.01)
*G01N 21/88* (2006.01)

(52) U.S. Cl.
CPC .......... *G06T 7/0004* (2013.01); *G01N 21/8806* (2013.01); *G06T 7/001* (2013.01); *G06T 7/0081* (2013.01); *G06T 7/0083* (2013.01); *G06T 7/0087* (2013.01); *G06T 7/0097* (2013.01); *G06T 2200/24* (2013.01); *G06T 2207/10024* (2013.01); *G06T 2207/20076* (2013.01); *G06T 2207/20092* (2013.01); *G06T 2207/20144* (2013.01); *G06T 2207/30164* (2013.01)

(58) Field of Classification Search
None
See application file for complete search history.

(56) References Cited

U.S. PATENT DOCUMENTS

| 2006/0018531 | A1  | 1/2006  | Murakami et al. |
| 2006/0018534 | A1* | 1/2006  | Nagata et al. ................. 382/164 |
| 2013/0329987 | A1* | 12/2013 | Gong ............................. 382/159 |

FOREIGN PATENT DOCUMENTS

JP    2006058284 A    3/2006

OTHER PUBLICATIONS

International Search Report issued in PCT/JP2012/071758 mailed on Oct. 23, 2012 (4 pages).
Boykov, Y. et al.; "Interactive Graph Cuts for Optimal Boundary & Region segmentation of Objects in N-D Images"; Proceedings of "Internation Conference on Computer Vision", Vancouver, Canada, Jul. 2001, vol. 1, pp. 105-112 (8 pages).

* cited by examiner

*Primary Examiner* — Atiba O Fitzpatrick
*Assistant Examiner* — David Perlman
(74) *Attorney, Agent, or Firm* — Osha Liang LLP

(57) ABSTRACT

An inspection area setting method for setting inspection area-defining information defining an inspection area to an image inspecting device, the image inspecting device being configured to extract a portion constituting the inspection area as an inspection area image from an original image obtained by taking an image of an inspection object, and to inspect the inspection object by analyzing the inspection area image, includes an acquisition step of acquiring a sample image obtained by taking an image of a sample of the inspection object, an inspection area searching step, and a setting step.

18 Claims, 11 Drawing Sheets

⇩ Automatic calculation of inspection area

⇩ Contour correcting tool, Make path of contour of inspection area

⇩ Correct control point

⇩ Convert area surrounded by path into inspection area

⇩ Contour drawing tool

Draw contour using free curve

⇩ Synthesize drawn contour

Arc converting tool

Designate three points

Substitute part of contour for arc connecting three points

⇩ Line converting tool

Designate two points

⇩ Substitute part of contour for line connecting two points

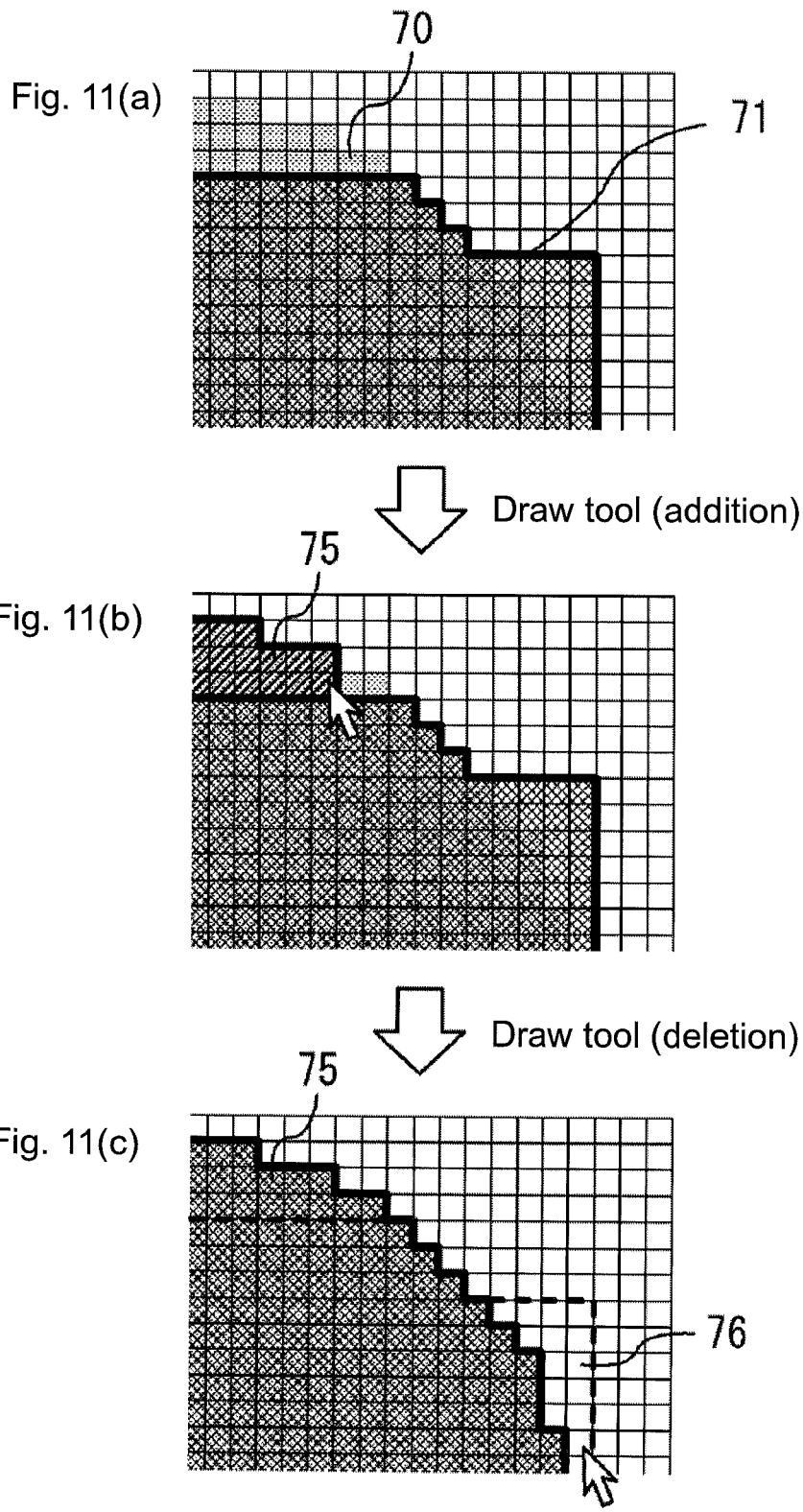

INSPECTION AREA SETTING METHOD FOR IMAGE INSPECTING DEVICE

BACKGROUND

1. Technical Field

The present invention relates to an image inspecting device that performs an appearance inspection using an image.

2. Related Art

An image inspecting device that performs an appearance inspection using an image is widely used for the purpose of automation and labor-saving of an inspection in a production line. There are various kinds and techniques of the appearance inspection. In a basic configuration of the appearance inspection, an image of an inspection object is taken with an image sensor (camera), a portion constituting an inspection area is extracted from the obtained image, and a feature of the image of the inspection area portion is analyzed and evaluated to perform an intended inspection (such as non-defective or defective determination, sorting, and information acquisition).

In this kind of image inspecting device, it is necessary to perform preparation work such as setting of the inspection area prior to inspection processing. A tool dedicated to the setting of the inspection area is prepared in a general device, and a user can properly set the inspection area according to an inspection object or an inspection purpose using the tool. However, the conventional tool has only a function of defining the inspection area using simple graphics such as a circle and a rectangle and a combination thereof. Accordingly, in the case that the inspection object has a complicated or special shape, sometimes the inspection area cannot correctly be matched with a contour of the inspection object. Even in the case that the contour of the inspection object can be expressed by the combination of the simple graphics, it takes a lot of time and workload to set the inspection area as the number of combined graphics increases. Nowadays there is a strong need to shorten arrangement time as much as possible for improvement of efficiency in multikind and small-quantity production. Therefore, it is undesirable to take a lot of trouble to set the inspection area. At the same time, in order to meet a complicated product shape and sophisticated and diversified inspection content, or in order to improve accuracy and reliability of the inspection, there is also a strong need to correctly set the inspection area only to a portion to be inspected.

Conventionally, an inspection area extracting technique in which binarization or color gamut extraction is used is well known as a technique of automatically setting the inspection area. In the inspection area extracting technique, a pixel group corresponding to a previously-set brightness range or color gamut is extracted from the image, and the pixel group is set to the inspection area. The inspection area extracting technique is effectively used in the case of a high brightness or color contrast between a portion (foreground) to be extracted as the inspection area and other portions (background). For example, the inspection area extracting technique is used in processing of extracting only an article portion from an image of an article conveyed on a belt conveyer.

A correct foreground portion is difficult to be solely extracted by the binarization or the color gamut extraction, when shade and shadow exist in the foreground portion to be extracted as the inspection area due to an influence of lighting, when the foreground portion is constructed with various kinds of brightness or colors, or when a color close to the foreground portion exists in the background. Nowadays, with the progress of the sophistication and diversification of the inspection content, frequently there is few color difference between the background and the foreground. The inspection directed only to one of cutting surfaces of a component having subjected to a forming-process and the inspection directed only to one of components mounted on a printed board can be cited as an example of few color difference between the background and the foreground. Because the binarization or the color gamut extraction is performed in each pixel of the image, the binarization or the color gamut extraction is easily influenced by a noise or a variation in lighting, and some pixel may be missing in the extracted inspection area or may be unnecessarily selected from the background like an enclave, which results in inspection accuracy being degraded.

Patent Document 1 discloses the inspection area setting methods such as a method for setting a position or a size of the inspection area from CAD data of an inspection object component and a method for recognizing an area to be inspected by taking a difference between two images taken before and after component mounting. Although the use of these inspection area setting methods can automatically set the inspection area, the inspection area setting methods lack versatility because application targets of the inspection area setting methods are restricted.

Patent Document

Patent Document 1: Japanese Unexamined Patent Publication No. 2006-58284

Non-Patent Document

Non-Patent Document 1: Y. Boykov and M.-P. Jolly: "Interactive Graph Cuts for Optimal Boundary & Region Segmentation of Objects in N-D images", ICCV2001, 01, p. 105 (2001)

SUMMARY

One or more embodiments of the present invention provides a technology of being able to simply and accurately set the inspection area even when the object has the complicated or special shape or when the color of the foreground is possibly confused with the color of the background.

According to one or more embodiments of the present invention, an optimal solution of the inspection area is searched by comprehensively evaluating color or brightness information and edge information with respect to the sample image of the inspection object, thereby automatically or semi-automatically setting the inspection area.

Specifically, an inspection area setting method for setting inspection area-defining information defining an inspection area to an image inspecting device, the image inspecting device being configured to extract a portion constituting the inspection area as an inspection area image from an original image obtained by taking an image of an inspection object, and to inspect the inspection object by analyzing the inspection area image, the inspection area setting method includes: an acquisition step in which a computer acquires a sample image obtained by taking an image of a sample of the inspection object; an inspection area searching step in which the computer obtains an optimal solution of the inspection area from a plurality of candidate areas by evaluating both pixel separation and edge overlap with respect to the plurality of candidate areas that are of candidate solutions of the inspection area based on information on color or brightness of each pixel in the sample image and information on an edge included in the sample image, the pixel separation being a degree of separation of the color or the brightness between an inside and an outside of each candidate area, the edge overlap being an overlap degree between an contour of each candidate area and the edge in the sample image; and a setting step in which the computer sets inspection area-defining information defining a position and a shape in the image of the inspection area obtained in the inspection area searching step to the image inspecting device.

According to the configuration, the position and the shape of the inspection area are decided by the optimal solution search in which the sample image is used. Therefore, compared with the conventional technique in which the inspection area is manually input using the simple graphics, the complicated or special shape can be dealt with while the setting time and the workload are significantly reduced. Additionally, both the pixel separation of the color or brightness between the inside and the outside of the inspection area and the edge overlap of the contour of the inspection area are comprehensively evaluated using the information on the edge in addition to the information on the color or the brightness, so that the area extraction accuracy can be improved compared with the conventional techniques such as the binarization and the color gamut extraction.

According to one or more embodiments of the present invention, the inspection area setting method further includes a parameter receiving step in which the computer receives input of a parameter from a user. In the inspection area setting method, every time the computer receives the input of the parameter from the user in the parameter receiving step, the computer performs the inspection area searching step with the input parameter as a constraint condition to recalculate the optimal solution of the inspection area, and displays the recalculated inspection area on a display device.

According to the configuration, the user can easily check whether the desired area is selected as the inspection area by seeing the inspection area displayed on the display device. For an improper inspection area, the recalculation result is instantly checked on the screen while the parameter is properly adjusted, so that the desired inspection area can easily be narrowed down.

According to one or more embodiments of the present invention, in the parameter receiving step, the user inputs a balance parameter as one kind of the parameter in order to adjust a balance between the pixel separation and the edge overlap, and in the inspection area searching step, weight are adjusted in evaluating the pixel separation and the edge overlap according to the balance parameter input from the user.

Even for the image in which the automatic cutting between the foreground and the background is hardly performed, the user adjusts the balance parameter, whereby the desired inspection area can simply be set in a short time.

According to one or more embodiments of the present invention, a value obtained by evaluating a likelihood of a foreground of the color or the brightness of each pixel inside the candidate area with respect to representative color or representative brightness of the foreground, a value obtained by evaluating a likelihood of a background of the color or the brightness of each pixel outside the candidate area with respect to representative color or representative brightness of the background, or a value obtained by synthesizing both the values is used as the pixel separation in the inspection area searching step.

According to the configuration, the pixel separation is evaluated to be high with increasing likelihood of the foreground of the pixel inside the inspection area and with increasing likelihood of the background of the pixel outside inspection area. The color or the brightness is decided as the representative of the foreground or the background, and the inspection area is searched based on the representative color or brightness. Therefore, a potential to reach an adequate solution can dramatically be enhanced. All or some of the pixels inside the candidate area may be used in calculating a value used to evaluate the likelihood of the foreground. Similarly, all or some of the pixels outside the candidate area may be used in calculating a value used to evaluate the likelihood of the background.

According to one or more embodiments of the present invention, in the inspection area searching step, the weight is adjusted in evaluating the pixel separation and the edge overlap such that the weight of the pixel separation increases with increasing difference between the representative color or the representative brightness of the foreground and the representative color or the representative brightness of the background, and such that the weight of the edge overlap increases with decreasing difference.

In the configuration, the user does not adjust the balance parameter, but the balance parameter is automatically adjusted to a proper value. Therefore, the potential to reach the adequate solution can be enhanced even in the absence of user aid.

In the parameter receiving step, when the user inputs the representative color or the representative brightness of the foreground, the background, or the both as one kind of the parameter, a potential to reach an adequate solution can further be enhanced.

At this point, according to one or more embodiments of the present invention, in the parameter receiving step, the sample image is displayed on the display device, the user designates a portion to be the foreground or the background on the displayed sample image, and the color or the brightness of the designated portion is acquired as the representative color or the representative brightness. According to the configuration, the representative color or brightness can easily and certainly be designated.

Any parameter may be provided as long as the parameter has an influence on the optimal solution search of the inspection area. For example, information expressing a feature such as the shape and the size of the inspection area, a position of the inspection area in the image, and a texture, a topology, an adjacent element, and an inclusive element of the inspection area may be provided as the parameter, and the solution of the inspection area may be searched such that a degree of similarity between the feature of the inspection area and the feature expressed by the parameter increases in addition to the pixel separation and the edge overlap. Thus, the potential to reach the adequate solution can further be enhanced by setting various features of the inspection area to a constraint condition.

It is conceivable that sometimes the adjustment of the parameter is not sufficient to obtain a desired inspection area, or that sometimes the adjustment of the parameter takes a long time for trial and error of the parameter. Therefore, according to one or more embodiments of the present invention, the inspection area setting method further includes an inspection area correcting step of displaying the inspection area obtained in the inspection area searching step on the display device and of correcting the shape of the inspection area according to a correction instruction input from the user. When the shape of the inspection area can be corrected, the portion that is hardly automatically extracted by the computing machine can be complemented by the user aid, and therefore the optimal inspection area can easily be obtained in a short time.

Various manipulation systems are conceivable to be used for correcting the inspection area. For example, a whole or a part of the contour of the inspection area may be approximated using a path of a Bezier curve or a spline curve and the user may correct the path. Therefore, the contour of the inspection area can easily be corrected to a desired shape. According to one or more embodiments of the present invention, the user draws a free curve, and the free curve and the inspection area are synthesized such that the free curve constitutes a part of the contour of the inspection area. According to one or more embodiments of the present invention, the user designates an interval of a part of the contour of the inspection area, and the contour of the designated interval is replaced with a straight line or an arc. According to one or more embodiments of the present invention, the pixel designated by the user is added to the inspection area or excluded from the inspection area in the inspection area correcting step.

According to one or more embodiments of the present invention, an image inspecting device performs at least any one of the above methods. According to one or more embodiments of the present invention, an inspection area setting device for the image inspecting device performs at least one of the above methods related to the inspection area setting. One or more embodiments of the present invention includes an image inspecting method for performing at least one of the pieces of processing, an inspection area setting method, a program configured to cause the computer to perform the methods, or a recording medium in which the program is recorded.

According to one or more embodiments of the present invention, the inspection area can simply and accurately be set, even when the object has the complicated or special shape or when the color of the foreground is possibly confused with the color of the background.

BRIEF DESCRIPTION OF THE DRAWINGS

FIGS. 11(a) to 11(c) are views illustrating an operation example of a draw tool.

DETAILED DESCRIPTION

Hereinafter, embodiments of the present invention will be described below with reference to the drawings. In embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid obscuring the invention.

One or more of the following embodiments relate to an image inspecting device that performs an appearance inspection using an image, particularly to an inspection area setting device that aids work to set an inspection area to the image inspecting device. The image inspecting device according to one or more embodiments of the present invention is used to continuously inspect many articles in an automatic or semi-automatic manner on an FA production line. In the image inspecting device of one or more of the embodiments, because the inspection is performed by extracting a predetermined inspection area from an original image taken with an image sensor, it is assumed that a position and a shape of an inspection area are fixed in the original image irrespective of the kind of the article as an inspection object. Although there are various purposes and inspection items for the appearance inspection, the inspection area setting device of one or more of the embodiments can be applied to any inspection. In one or more of the embodiments, the inspection area setting device is mounted in a form of one function (setting tool) of the image inspecting device. Alternatively, the image inspecting device and the inspection area setting device may separately be formed.

<First Embodiment>
(Image inspecting device)

Figure 1:
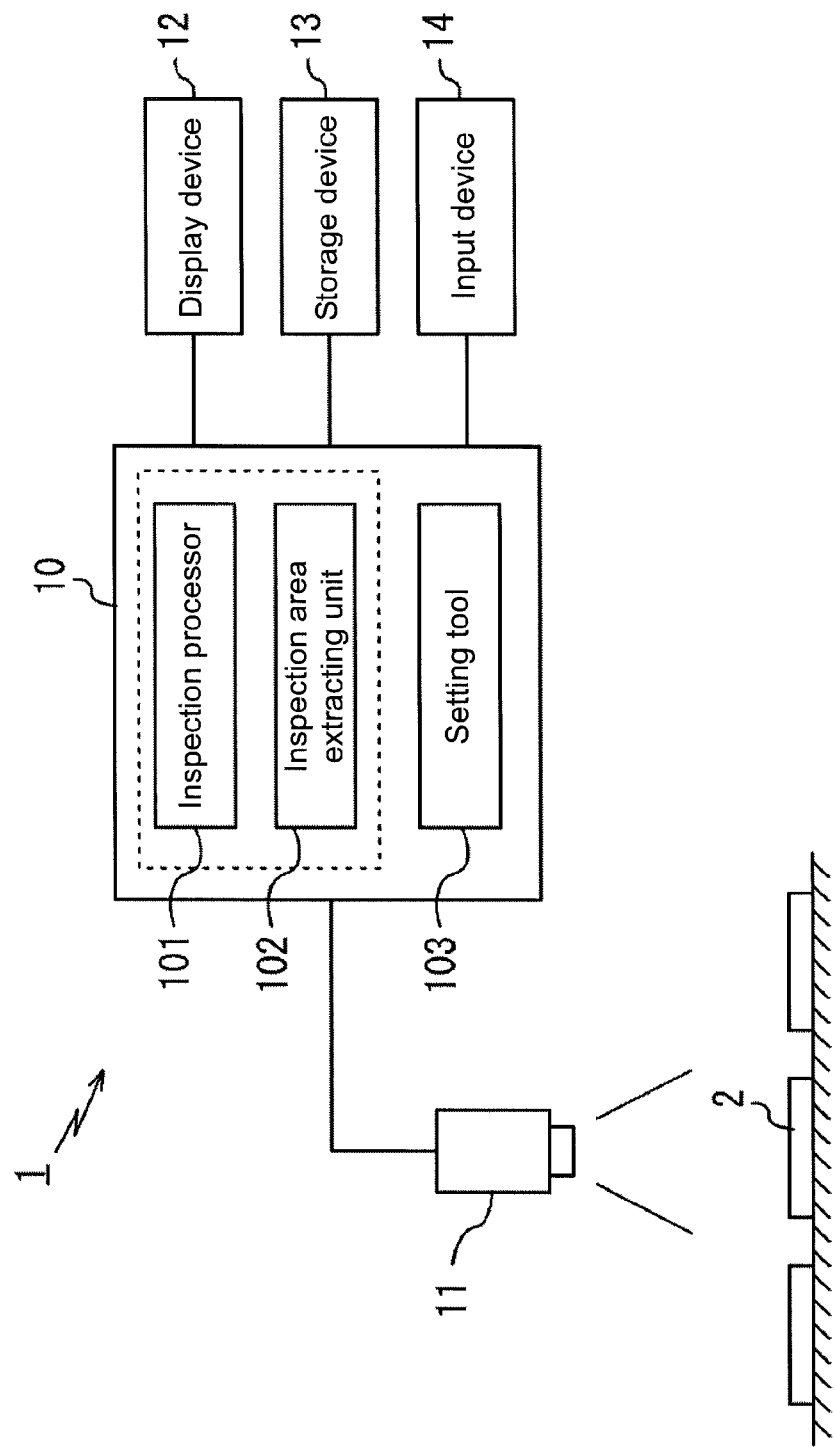
FIG. 1 is a diagram schematically illustrating a configuration of an image inspecting device.

FIG. 1 is a diagram schematically illustrating a configuration of an image inspecting device. Image inspecting device 1 is a system that performs the appearance inspection of inspection object 2 conveyed on a conveying path.

As illustrated in FIG. 1, image inspecting device 1 includes pieces of hardware such as device body 10, image sensor 11, display device 12, storage device 13, and input device 14. Image sensor 11 is a device that captures a color or monochrome still or moving image in device body 10. For example, according to one or more embodiments of the present invention, a digital camera can be used as image sensor 11. However, in the case that not a visible-light image but special images (such as an X-ray image and a thermo image) are used, a sensor may be used according to the special image. Display device 12 is one that displays a GUI screen related to the image captured with image sensor 11, an inspection result, inspection processing, and setting processing. For example, a liquid crystal display can be used as display device 12. Storage device 13 is one in which various pieces of setting information (such as inspection area-defining information and inspection logic) referred to by image inspecting device 1 during the inspection processing and the inspection result are stored. For example, an HDD, an SSD, a flash memory, and a network storage can be used as storage device 13. Input device 14 is one that is operated by a user in order to input an instruction to device body 10. For example, a mouse, a keyboard, a touch panel, and a dedicated console can be used as input device 14.

Device body 10 can be constructed with a computer that includes a CPU (Central Processing Unit), a main storage device (RAM), and auxiliary storage device (such as a ROM, the HDD, and the SSD) as hardware. Device body 10 includes inspection processor 101, inspection area extracting unit 102, and setting tool 103 as functions. Inspection processor 101 and inspection area extracting unit 102 are the function related to the inspection processing, and setting tool 103 is the function of aiding user work to set setting information necessary for the inspection processing. These functions are implemented in a manner such that a computer program stored in the auxiliary storage device or storage device 13 is loaded on the main storage device and executed by the CPU. FIG. 1 illustrates only an example of a device configuration. Alternatively, all or some of image sensor 11, display device 12, storage device 13, and input device 14 may be integral with device body 10. Device body 10 may be constructed with a personal computer or a slate computer, or may be constructed with a dedicated chip or an on-board computer.

(Inspection Processing)

Figure 2:
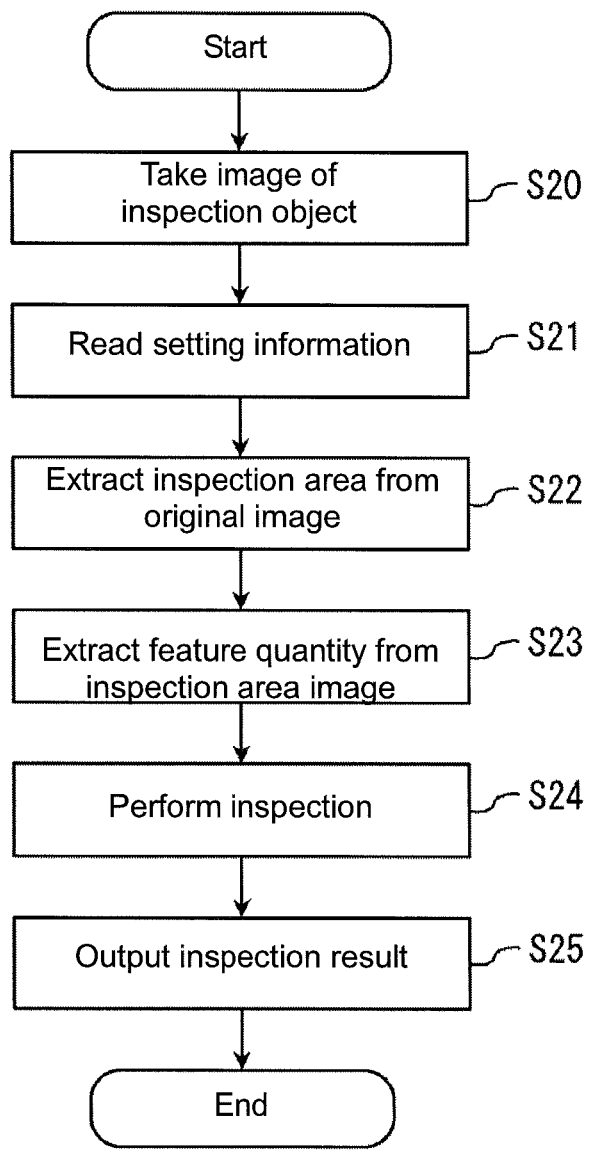
FIG. 2 is a flowchart illustrating a flow of inspection processing.
Figure 3:
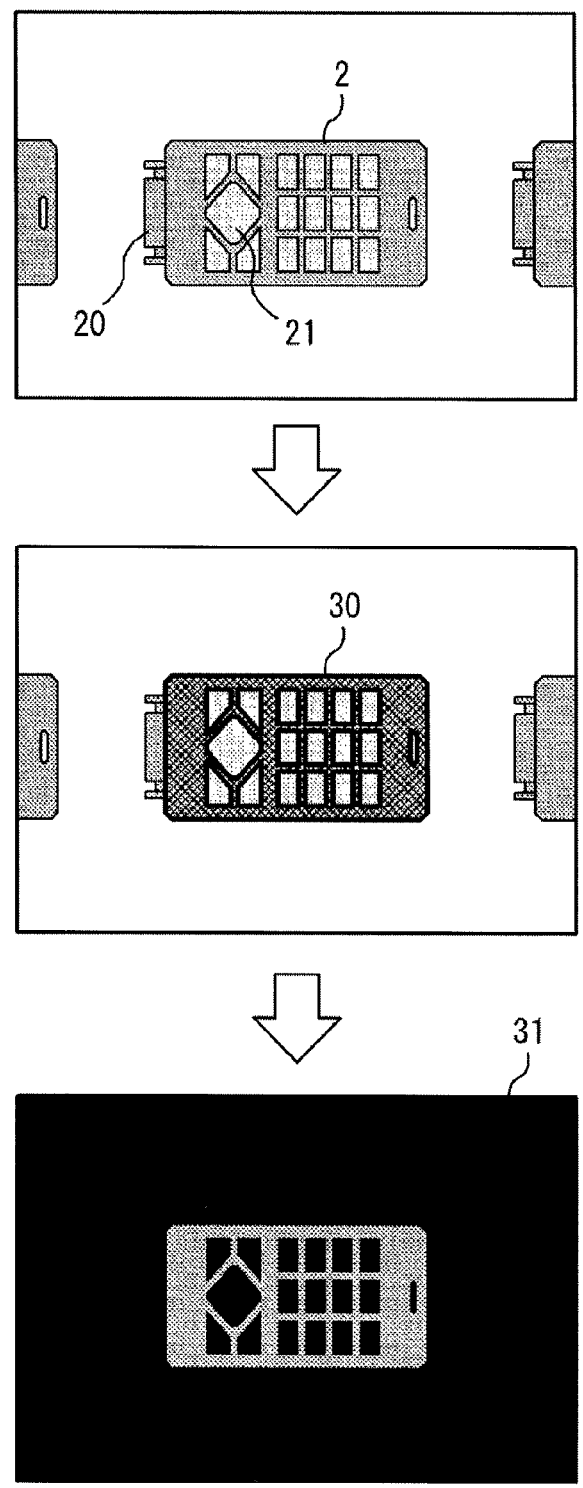
FIG. 3 shows views illustrating an inspection area extracting process in the inspection processing.

An operation related to the inspection processing by image inspecting device 1 will be described with reference to FIGS. 2 and 3. FIG. 2 is a flowchart illustrating a flow of the inspection processing, and FIG. 3 shows views illustrating an inspection area extracting process in the inspection processing. For the sake of convenience, the flow of the inspection processing is described by taking an inspection (detection of a flaw and color unevenness) of a panel surface of a chassis component in a mobile phone as an example.

In Step S20, image sensor 11 takes an image of inspection object 2, and image data is captured by device body 10. At this point, the captured image (original image) is displayed on display device 12 as needed basis. An upper stage of FIG. 3 illustrates an example of the original image. The image of chassis component 2 as the inspection object is taken in a center of the original image, and images of adjacent chassis components on the conveying path are partially taken on right and left of the chassis component of the inspection object.

In Step S21, inspection area extracting unit 102 reads necessary setting information from storage device 13. The setting information includes at least the inspection area-defining information and the inspection logic. The inspection area-defining information is one that defines the position and the shape of the inspection area to be extracted from the original image. The inspection area-defining information has any form. For example, a bit mask in which a label is changed between inside and outside the inspection area and vector data in which a contour of the inspection area is expressed by a Bezier curve or a spline curve can be used as the inspection area-defining information. The inspection logic is information that defines a content of the inspection processing. For example, the kind of the feature quantity used in the inspection, a determination method, and a parameter and a threshold used in feature quantity extraction or determination processing correspond to the inspection logic.

In Step S22, inspection area extracting unit 102 extracts the possible inspection area from the original image according to the inspection area-defining information. A middle stage of FIG. 3 illustrates a state in which inspection area (indicated by cross-hatching) 30 defined by the inspection area-defining information is superimposed on the original image. It is found that inspection area 30 is just superimposed on the panel surface of chassis component 2. A lower stage of FIG. 3 illustrates a state in which the image (inspection area image 31) of inspection area 30 is extracted from the original image. The conveying path and adjacent components seen in the previous images around chassis component 2 are deleted in inspection area image 31. Hinge portion 20 and button portion 21, which are excluded from a target region of the surface inspection, are also deleted. Obtained inspection area image 31 is transferred to inspection processor 101.

In Step S23, inspection processor 101 extracts the necessary feature quantity from inspection area image 31 according to the inspection logic. In the first embodiment, colors of pixels of inspection area image 31 and an average value thereof are extracted as the feature quantity in order to inspect the flaw and the color unevenness of the surface.

In Step S24, inspection processor 101 determines the existence or non-existence of the flaw and the color unevenness according to the inspection logic. For example, in the case that a pixel group in which a color difference from the average value obtained in Step S23 exceeds a threshold, inspection processor 101 can determine the pixel group to be the flaw or the color unevenness.

In Step S25, inspection processor 101 displays the inspection result on display device 12, or stores the inspection result in storage device 13. Therefore, the inspection processing is completed for one inspection object 2. In the production line, the pieces of processing in Steps S20 to S25 of FIG. 2 are repeated in synchronization with the conveyance of inspection object 2 to an angle of view of image sensor 11.

In the appearance inspection, desirably only the pixels to be inspected are cut out as inspection area image 31 in just proportion. When a background portion or an excess portion (in the example of FIG. 3, hinge portion 20 and button portion 21) is included in inspection area image 31, the pixels of the background portion or the excess portion cause a noise to possibly degrade inspection accuracy. On the other hand, when inspection area image 31 is smaller than a range to be inspected, there is a risk of generating omission of the inspection. Therefore, in image inspecting device 1 of the first embodiment, setting tool 103 is prepared in order to simply produce the inspection area-defining information cutting out the accurate inspection area image.

(Inspection Area Setting Processing)

Figure 4:
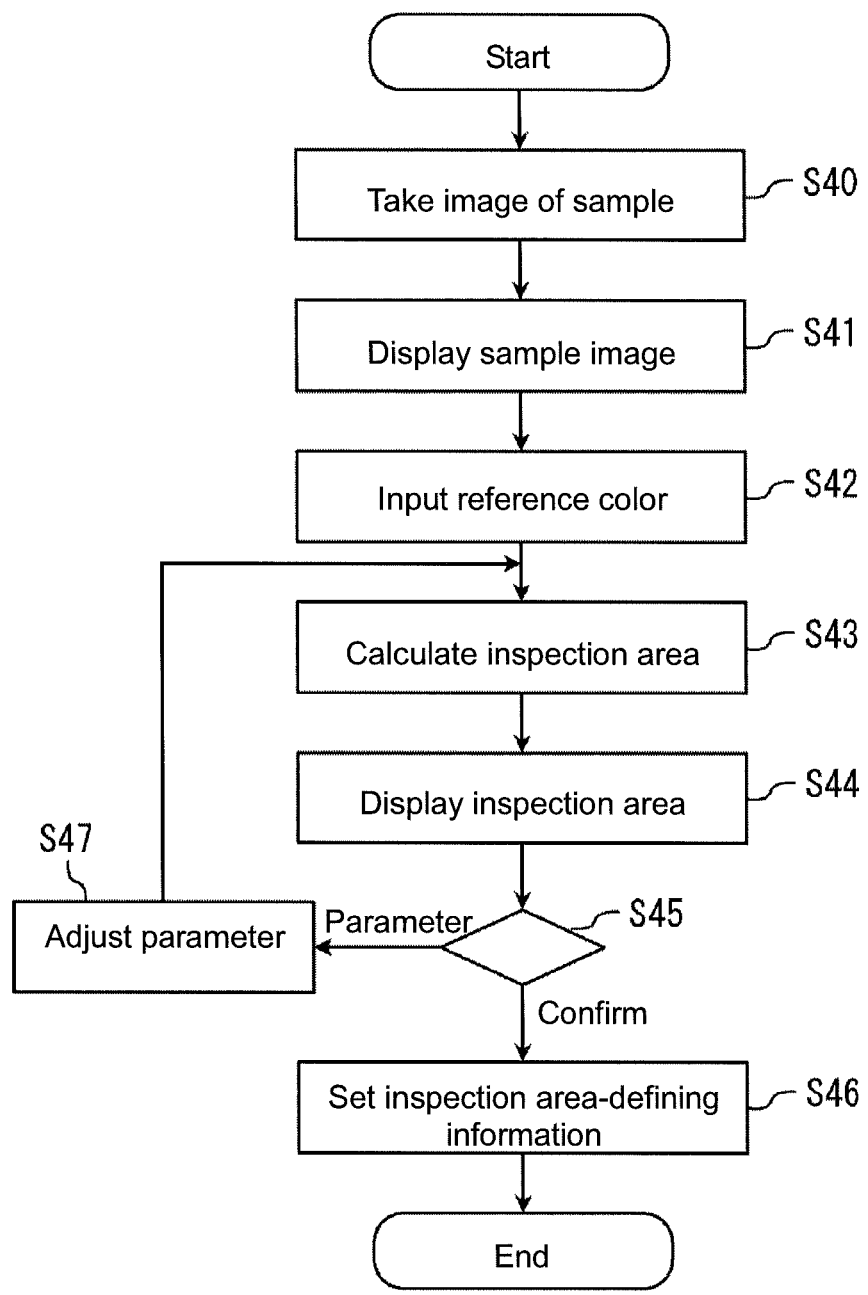
FIG. 4 is a flowchart illustrating a processing flow for setting an inspection area using setting tool 103.

The function and the operation of setting tool 103 will be described with reference to FIGS. 4 and 5. FIG. 4 is a flowchart illustrating a processing flow for setting the inspection area using setting tool 103, and FIG. 5 is a view illustrating an example of an inspection area setting screen.

Figure 5:
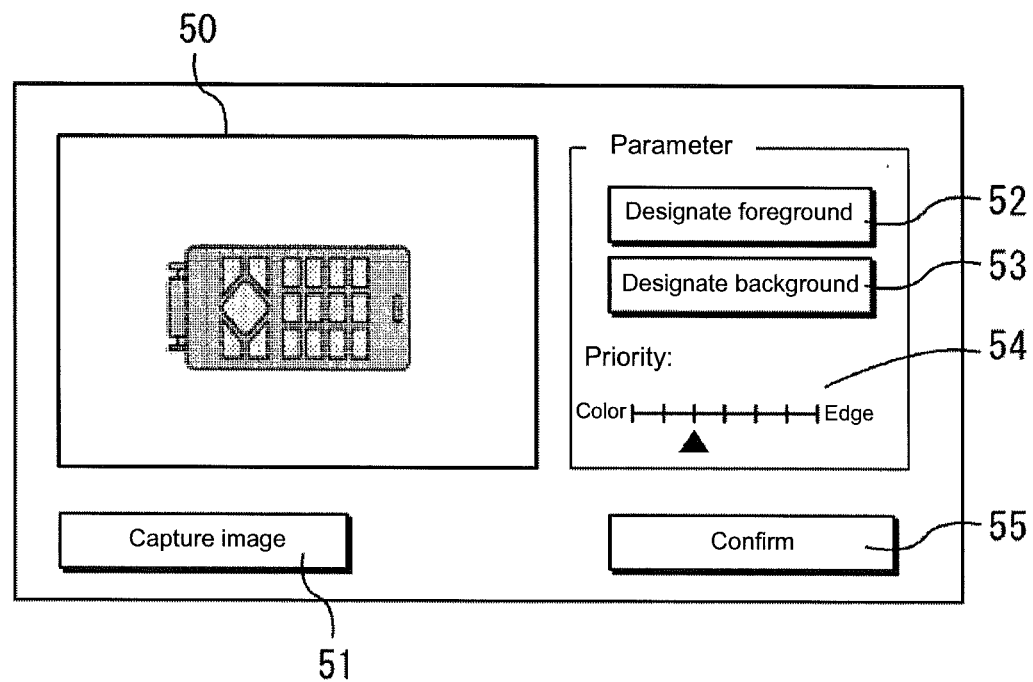
FIG. 5 is a view illustrating an example of an inspection area setting screen.

When setting tool 103 is started up, a setting screen in FIG. 5 is displayed on display device 12. Image window 50, image capturing button 51, foreground designating button 52, background designating button 53, priority adjusting slider 54, and confirm button 55 are provided in the setting screen. Manipulations such as selection of a button and movement of a slider can be performed using input device 14. The setting screen is illustrated only by way of example. Any UI may be used as long as the parameter can be input or the inspection area can be checked as described later.

When image capturing button 51 is pressed, setting tool 103 takes an image of a sample of the inspection object with image sensor 11 (Step S40). A non-defective inspection object (in the example, the chassis component) is used as the sample, and the image of the sample is taken in the same state (for example, regarding illumination and a relative position between image sensor 11 and sample) as the actual inspection processing. The obtained sample image data is captured in device body 10. In the case that the previously-taken sample image exists in the auxiliary storage device or storage device 13 of device body 10, setting tool 103 may read the data of the sample image from the auxiliary storage device or storage device 13.

The sample image obtained in Step S40 is displayed in image window 50 of the setting screen as illustrated in FIG. 5 (Step S41).

In Step S42, the user inputs representative colors (in the case of the monochrome image, representative brightness) of a foreground and a background. The foreground indicates a portion that should be extracted as the inspection area, and the background indicates a portion except the inspection area. In the case that the user inputs the representative color of the foreground, the user presses foreground designating button 52 to change the setting screen to a foreground designating mode, and designates a portion that should be set to the foreground on the sample image displayed in image window 50. At this point, because the designation is made to pick up the representative color of the foreground, some pixels or a pixel group on the panel surface of the chassis component may properly be selected in the example of FIG. 5. When a largely different pattern, shade and shadow, or color portion is included in the foreground, according to one or more embodiments of the present invention, the pixel group is selected such that related colors are covered as much as possible. In the case that the user inputs the representative color of the background, the user presses background designating button 53 to change the setting screen to a background designating mode, and performs the similar manipulation. It is not always necessary to input the representative colors of the foreground and the background. Only one of the foreground and the background may be input, or Step S42 may be eliminated in the case that the representative color is already known or in the case that the representative color can automatically be calculated from a color distribution of the sample image.

In Step S43, based on the representative colors of the foreground and the background that are designated in Step S42, setting tool 103 separates (segments) the sample image into the foreground and the background and selects the foreground portion as the inspection area. In the first embodiment, using information on an edge included in the sample image in addition to information on the color of each pixel of the sample image, both a degree of color separation (hereinafter referred to as pixel separation) between the foreground and the background (that is, between the inside and the outside of the candidate area) and a degree of overlap (hereinafter referred to as edge overlap) between a boundary of the foreground and the background (that is, the contour of the candidate area) and the edge in the sample image are comprehensively evaluated with respect to the plurality of candidate areas that are of candidate solutions of the inspection area, and an optimal solution is searched such that both the pixel separation and the edge overlap are enhanced. A method for calculating the inspection area is described later in detail.

In Step S44, the inspection area calculated in Step S43 is displayed on image window 50 of the setting screen. The user can check whether the desired area is selected as the inspection area by seeing the inspection area displayed on the setting screen. At this point, when the inspection area is overlaid on the sample image, according to one or more embodiments of the present invention, the inspection object and the inspection area are easily compared to each other.

Then setting tool 103 waits for the input from the user (Step S45). In the case that confirm button 55 is pressed, setting tool 103 generates inspection area-defining information on the current inspection area and stores the inspection area-defining information in storage device 13 (Step S46). On the other hand, in the case that the improper inspection area is displayed on the setting screen, the user can adjust the parameter by manipulating foreground designating button 52, background designating button 53, and priority adjusting slider 54 (Step S47). Re-designation of the representative color of the foreground or the background has an influence on the evaluation of the pixel separation. When a priority between the color information and the edge information is changed using priority adjusting slider 54, a balance (weight) can be changed in evaluating the pixel separation and the edge overlap. When receiving the input (change) of the parameter from the user, setting tool 103 recalculates the optimal solution of the inspection area with the new parameter as a constraint condition, and displays the post-recalculation inspection area on the setting screen (Step S47→Steps S43 and S44). Therefore, while the parameter is properly adjusted, the calculation of the inspection area can be repeated until the desired result is obtained.

Figure 6:
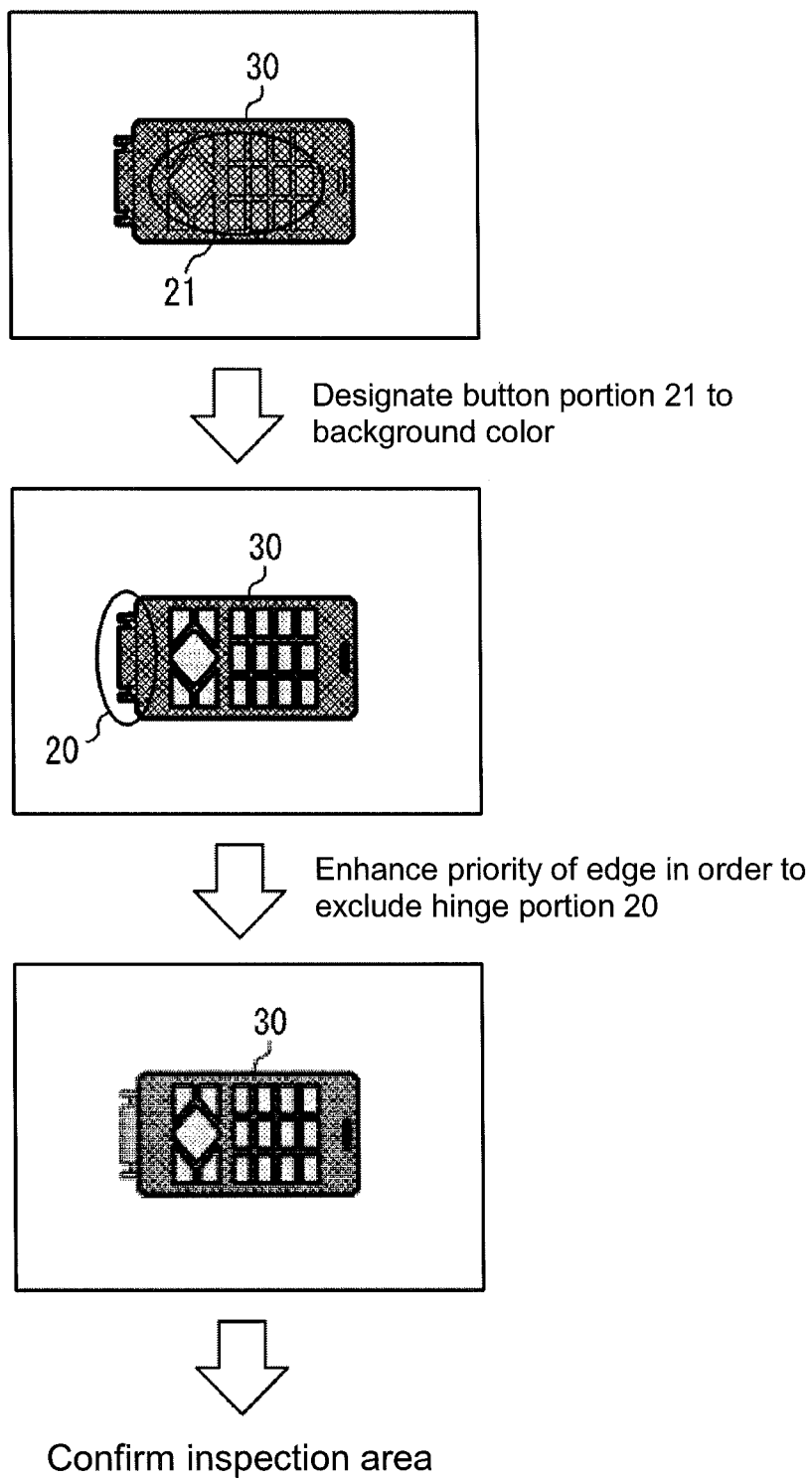
FIG. 6 shows views exemplifying a process of narrowing down the inspection area by parameter adjustment.

FIG. 6 shows views exemplifying a process of narrowing down the inspection area by parameter adjustment. An upper stage of FIG. 6 illustrates inspection area 30 obtained by the initial calculation. In the initial calculation result, hinge portion 20 and button portion 21 of the chassis component are also included in inspection area 30. However, hinge portion 20 and button portion 21 are desired to be excluded from the inspection area because the inspection for the flaw and the color unevenness inspection is directed to the panel surface (see FIG. 3). Therefore, the user first presses background designating button 53 to change the setting screen to the background designating mode, and additionally designates the color of button portion 21 in the sample image to the representative color of the background. Therefore, button portion 21 is excluded from inspection area 30 as illustrated in the image example of the middle stage in FIG. 6. Then, hinge portion 20 is dealt with by adjusting a balance parameter because hinge portion 20 has a little color difference with the panel surface. That is, by focusing on the edge in a step between hinge portion 20 and the panel surface, the priority of the edge information is enhanced using priority adjusting slider 54. Therefore, as illustrated in the image example of the lower stage in FIG. 6, the contour of inspection area 30 is set to the edge between hinge portion 20 and the component surface to form desired inspection area 30.

(Calculation of Inspection Area)

The inspection area calculating method in Step S43 of FIG. 4 will be described below.

As described above, in setting tool 103 of the first embodiment, the optimal solution is obtained from the candidate solutions of the inspection area by comprehensively evaluating both the pixel separation between the foreground and the background and the edge overlap of the boundary of the foreground and the background. The calculation can be considered as an optimization problem that minimizes (or maximizes) an objective function including a function evaluating the pixel separation based on the color information and a function evaluating the edge overlap based on the edge information. A technique of solving the optimization problem of the inspection area using a graph cut algorithm will be described below. Because the graph cut algorithm is a well-known technique (see Non-Patent Document 1), the description of a basic concept of the graph cut algorithm is neglected, and a portion unique to the first embodiment is mainly described.

In the graph cut algorithm, as indicated by the following equation, an energy function is defined as the objective function, and solution L minimizing energy E is obtained when I is provided. In the first embodiment, I is the sample image, and L is a label (that is, the inspection area) indicating the foreground or the background.

[Mathematical formula 1]

$$E(L \mid I) = \sum_{i \in \Omega} U(l_i \mid I) + \lambda \sum_{\{i,j\} \in N} V(l_i, l_j \mid I) \quad (1)$$

Where i and j are indexes of the pixel, $\Omega$ is a pixel group in the image I, and N is an adjacent pixel pair group in the image I. li and lj are designated labels of the pixels i and j. It is assumed that a label of "1" is provided for the foreground, and that a label of "0" is provided for the background. A first term of the right side is called a data term, and provides the constraint condition related to a target pixel i. A second term of the right side is called a smoothing term, and provides the constraint condition related to the pixels i and j adjacent to each other. $\lambda$ is a balance parameter deciding the weights of (balance between) the data term and the smoothing term.

The data term is defined by the function evaluating the pixel separation based on the color information. For example, an evaluation function U of the data term may be defined by the following equation.

[Mathematical formula 2]

$$U(l_i \mid I) = \begin{cases} -\log p(I \mid l_i = 1), & \text{if } l_i = 1 \\ -\log p(I \mid l_i = 0), & \text{if } l_i = 0 \end{cases} \quad (2)$$

Where $-\log p(I|li=1)$ is a function (logarithmic likelihood) expressing a likelihood of the foreground of a foreground pixel (a pixel on which the foreground label of "1" is put) with respect to the foreground representative color, and is called a foreground likelihood. A function estimated from the foreground representative color (for example, the color distribution of the foreground representative color is approximated by a Gaussian mixture model) is used as a probability density function in the foreground likelihood. On the other hand, $-\log p(I|li=0)$ is a function (logarithmic likelihood) expressing a likelihood of the background of a background pixel (a pixel on which the background label of "0" is put) with respect to the background representative color, and is called a background likelihood. A function estimated from the background representative color (for example, the color distribution of the background representative color is approximated by the Gaussian mixture model) is used as a probability density function in the background likelihood. That is, the data term expresses a summation of the foreground likelihoods of the foreground pixels and the background likelihoods of the background pixels, the energy decreases as the color of the foreground pixel comes closer to the foreground representative color and as the color of the background pixel comes closer to the background representative color, and the energy increases as the color of the foreground pixel is further separated from the foreground representative color and as the color of the background pixel is further separated from the background representative color.

The smoothing term is defined by a function evaluating the edge overlap based on the edge information. For example, an evaluation function V of the smoothing term can be defined by the following equation.

$$V(l_i, l_j \mid I) = \begin{cases} \exp\{-\beta \|l_i - l_j\|^2\}, & \text{if } l_i \neq l_j \\ 0, & \text{if } l_i = l_j \end{cases} \quad \text{[Mathematical formula 3]}$$

Where li and lj are pixel values (color or brightness) of the pixels i and j and β is a coefficient. $\|li-lj\|^2$ expresses a difference (distance) between the pixel values on a predetermined color space, namely, a height of contrast between the pixels.

According to the above equation, in the case that the adjacent pixels i and j differ from each other in the label, the energy increases with decreasing contrast between the pixels i and j, and the energy decreases with increasing contrast. The portion having the high contrast between the adjacent pixels is one in which the color or the brightness changes largely in the image, namely, the edge portion in the image. That is, in the equation, the energy decreases as larger portions of the boundary (pixel pair having different labels) of the foreground and the background overlaps the edge in the image.

A global minimum exists in the above energy function when submodularity is satisfied. Similarly, when a term satisfying the submodularity is added, the global minimum can be obtained with the constraint condition. Because a well-known search algorithm may be used to efficiently solve the global minimum, the detailed description is neglected.

In the parameters that can be adjusted on the setting screen, "the foreground representative color" and "the background representative color" have an influence on the value of the data term. "The priority between the color information and the edge information" corresponds to the balance parameter λ. When the user enhances the priority of the color information, the weight of the data term is increased by decreasing the value of the parameter λ. When the user enhances the priority of the edge information, the weight of the smoothing term is increased by increasing the value of the parameter λ. The value of the parameter λ can also automatically be decided by a computing machine (setting tool 103). For example, setting tool 103 calculates the difference between the foreground representative color and the background representative color, and the weight of the data term is increased by decreasing the value of the parameter λ in the case of the large difference. This is because the data term has high reliability in the case of the clear color difference between the foreground and the background. On the other hand, the weight of the smoothing term is increased by increasing the value of the parameter λ in the case of the small difference between the foreground representative color and the background representative color. This is because area segmentation based on the edge information tends to provide a good result rather than based on the color information in the case of the unclear color difference between the foreground and the background. Thus, the potential to reach an adequate solution can be enhanced in the absence of user aid by automatically adjusting the balance parameter λ. According to one or more embodiments of the present invention, the initial value of the balance parameter λ is automatically decided by the above method, and the user may adjust the balance parameter λ, (the priority between the color information and the edge information) with the initial value as a starting point. This is because, with increasing adequacy of the initial value, the number of trial-and-error times of the user can be decreased and a workload on the parameter adjustment can be expected to be reduced.

In the equation (2), the summation of the likelihoods of the foregrounds of the foreground pixel (foreground likelihood) and the likelihoods of the backgrounds of the background pixel (background likelihood) is used as the data term. However, the evaluation function of the pixel separation is not limited to the summation. For example, a product of the foreground likelihood and the background likelihood, a weighted sum, a weighted product, a non-linear function sum, and a non-linear function product may be used as the data term. A monotonically increasing function may be used as the non-linear function. A function in which both the foreground likelihood and the background likelihood are not evaluated but only one of the foreground likelihood and the background likelihood is evaluated can be used as the pixel separation. Specifically, a function in which $U(li|I)$ becomes zero for li=0 (or li=1) can be used in the equation (2). The following equation (4) is a function evaluating only the foreground likelihood.

$$U(l_i \mid I) = \begin{cases} -\log p(I \mid l_i = 1), & \text{if } l_i = 1 \\ 0, & \text{if } l_i = 0 \end{cases} \quad \text{[Mathematical formula 4]}$$

Either all the foreground pixels (that is, all the pixels inside the candidate area) or only some foreground pixels may be used to calculate the foreground likelihood. Similarly, either all the background pixels (that is, all the pixels outside the candidate area) or only some background pixels may be used to calculate the background likelihood. For example, a calculation time can be shortened by excluding the pixel in which the label is fixed from the calculation or by using only the pixel existing within a predetermined distance from the contour of the candidate area.

The function evaluating the foreground likelihood or the background likelihood is not limited to the equation (2). For example, a likelihood ratio that is of a ratio of the foreground likelihood to the background likelihood can be used as expressed by the following equation.

$$U(l_i \mid I) = \begin{cases} -\log \dfrac{p(I \mid l_i = 1)}{p(I \mid l_i = 0)}, & \text{if } l_i = 1 \\ -\log \dfrac{p(I \mid l_i = 0)}{p(I \mid l_i = 1)}, & \text{if } l_i = 0 \end{cases} \quad \text{[Mathematical formula 5]}$$

Using directly a histogram of the pixel group that is designated as the foreground representative color by the user (without estimating the probability density function), the foreground likelihood may be evaluated based on a similarity of color of each pixel with respect to the histogram of the foreground representative color, or the background likelihood may be evaluated based on a dissimilarity of color of each pixel with respect to the histogram of the foreground representative color. Similarly, the background likelihood may be evaluated based on a similarity with respect to a histogram (a histogram of the background representative color) of the pixel group that is designated as the background representative color by the user, or the foreground likelihood may be evaluated based on a dissimilarity with respect to the histogram of the background representative color. Alternatively, the similarity or the dissimilarity between a foreground histogram obtained from the foreground pixel group or a background histogram obtained from the background pixel group of the candidate area and the histogram of the foreground representative color or the histogram of the background representative color may be calculated using a predetermined function or a distance index. Alternatively, a histogram may be approximated from the information on the color or the brightness of the pixel group to calculate the similarity or the dissimilarity using the approximated histogram.

(Additional Parameter)

The three parameters of the foreground representative color, the background representative color, and the priority between the color information and the edge information are described above in the first embodiment. Additionally, any parameter may be used as long as the parameter can have an influence on the optimal solution search of the inspection area. For example, frequently the shape, the texture, the topology of the inspection area, the element adjacent to the inspection area, and the element included in the inspection area have the feature because the appearance inspection is mainly aimed at industrial products. The image sensor is installed such that the inspection object is fitted into the angle of view, so that the size of the inspection area or the position in the image of the inspection area can be predicted to some extent. Therefore, by inputting the information expressing the feature of the inspection area as the parameter by the user, and adding the constraint condition that evaluates the similarity between the feature provided by the parameter and the feature of the inspection area to the objective function, the potential to search the adequate inspection area is further enhanced.

A basic shape (such as a circle, a quadrangle, a triangle, and a star) of the inspection area and the feature (such as a linear outer shape, a round outer shape, and a jagged shape) of the contour can be used as shape information expressing the feature related to the shape of the inspection area. As to a UI used to input the shape information, template of the basic shapes or the features of the contours are listed, and the user may select the corresponding item. For example, in the case that the template of the basic shape is designated, the following expression may be inserted as the constraint condition.

$$\min \log \sum_i \| l_i - T(t_i) \|^2 \quad \text{[Mathematical formula 6]}$$

Where li is a designated label of the pixel i and ti is a label of a point corresponding to the pixel i on the template. T( ) expresses an affine transform. The above expression expresses a manipulation in which template matching is performed to the candidate area while the designated template is enlarged/reduced, rotated, and deformed and thereby calculating the minimum score. That is, the energy of the area having the shape closer to the basic shape designated by the user is decreased by the addition of the constraint condition, and the area is preferentially selected as the optimal solution.

For example, in the case that jaggedness or smoothness is designated as the feature of the contour, the following expression may be inserted as the constraint condition.

$$\log \left\{ \left\| \sum \left| \dfrac{\partial \theta}{\partial S} \right| - C \right\|^2 \right\} \quad \text{[Mathematical formula 7]}$$

Where S is a point on the contour of the foreground area, $\theta$ is a gradient angle of the contour, and $\partial \theta / \partial S$ expresses an amount of change of the gradient angle along the contour of the foreground area. C is a constant indicating the jaggedness (smoothness) designated by the user, and the value C increases with increasing jaggedness while the value C decreases with increasing smoothness. The above expression is a function evaluating whether a total value (expressing the jaggedness of the contour) of the amounts of change in the gradient angle along the contour of the foreground area is close to the value C (expressing the jaggedness designated by the user). That is, the area having the contour feature closer to the jaggedness designated by the user is preferentially selected as the optimal solution by the addition of the constraint condition.

An area, a vertical length, and a horizontal length of the inspection area can be used as size information expressing the feature related to the size of the inspection area. For example, in the case that the area is input as the size information, the following expression may be inserted as the constraint condition.

$$\log \left\{ \left\| \sum_i l_i - C \right\|^2 \right\} \quad \text{[Mathematical formula 8]}$$

Where C is the area (the number of pixels) of the foreground area designated by the user. Because of the foreground label of 1 and the background label of 0, $\Sigma l_i$ expresses the total number of the foreground pixels, namely, the area of the foreground area. Accordingly, the above expression is a function evaluating whether the area of the foreground area is close to the area C designated by the user. The area having the size closer to the area designated by the user is preferentially selected as the optimal solution by the addition of the constraint condition.

Centroid coordinates of the inspection area and an existence range (such as up, down, right, left, and center) of the inspection area can be used as position information expressing the feature related to the position in the image of the inspection area. For example, in the case that the centroid coordinates are input as the position information, the following expression may be inserted as the constraint condition.

$$\log\{\|w-C\|^2\} \qquad \text{[Mathematical formula 9]}$$

Where w is centroid coordinates of the foreground area and C is centroid coordinates designated by the user. The above expression is a function evaluating whether the centroid coordinates of the foreground area are close to the coordinates C designated by the user. The area having the centroid at the position closer to the coordinates designated by the user is preferentially selected as the optimal solution by the addition of the constraint condition.

Information expressing a pattern, shading of the color, irregularity, or a material in the inspection area can be used as texture information expressing the feature related to the texture of the inspection area. For example, various texture templates are listed, and the user may select a corresponding texture template from the list. For example, in the case that the texture template is input, the following expression may be input as the constraint condition.

$$\log f(h_{l=1}(I)-h_{l=1}(E)) \qquad \text{[Mathematical formula 10]}$$

Where I is a sample image and E is a texture template designated by the user. A color histogram of the foreground pixel is expressed by $h_{l=1}(\ )$ and a function indicating a similarity between the histograms is expressed by $f(\ )$. That is, the above expression is a function evaluating whether the color histogram of the foreground area in the sample image is similar to the color histogram of the texture designated by the user. The area having the texture similar to the texture designated by the user is preferentially selected as the optimal solution by the addition of the constraint condition.

(Advantage of First Embodiment)

According to setting tool 103 of the first embodiment, the position and the shape of the inspection area are decided by the optimal solution search in which the sample image is used. Therefore, compared with the conventional technique of manually inputting the inspection area using the simple graphics, the setting time and the workload can significantly be reduced, and the complicated shape and the special shape can be dealt with. Both the pixel separation of the color or the brightness between the inside and the outside of the inspection area and the edge overlap of the contour of the inspection area and the edge are comprehensively evaluated using the information on the edge in addition to the information on the color or the brightness, which allows the area extraction accuracy to be improved compared with the conventional technique such as the binarization and the color gamut extraction.

In setting tool 103 of the first embodiment, the user can arbitrarily select the priority between the color information and the edge information on the setting screen. For example, according to one or more embodiments of the present invention, the higher priority is put on the information on the color or the brightness rather than the information on the edge in the case that the image includes many pseudo-contours as in a case that a pattern is included in the foreground or the background. Whereas, according to one or more embodiments of the present invention, the higher priority is put on the information on the edge in the case of the image in which the color of the foreground is similar to the color of the background. For the image in which the foreground and the background are hardly separated from each other, it is very difficult to find the answer by the completely automatic method. At the same time, when seeing the image, the user can easily determine which one of the information on the color or the brightness and the information on the edge should have the higher priority, and the user can narrow down the parameter by trial and error. Accordingly, the balance parameter can be adjusted, whereby the desired inspection area can simply be set in a short time.

<Second Embodiment>

A second embodiment of the present invention will be described below. In the setting tool of the first embodiment, the inspection area can be narrowed down by adjusting the parameters such as the foreground and background representative colors and the priority between the color and the edge. However, only the adjustment of the parameter generates a risk that the user cannot reach the shape of the inspection area intended (some errors are left), and possibly it takes a long time to perform the trial and error of the parameter only by the adjustment of the parameter. Therefore, an inspection area correcting function that the user can interactively correct the shape of the inspection area after the inspection area is obtained by the calculation is provided in a setting tool of the second embodiment.

Hereinafter, (1) a contour correcting tool, (2) a contour drawing tool, (3) an arc converting tool, (4) a line converting tool, and (5) a draw tool will be described as examples of the inspection area correcting function provided by the setting tool of the second embodiment. For example, these tools can be started up from the setting screen in FIG. 5. The configuration of the image inspecting device, the operation of the inspection processing, and the operation of the automatic calculation (optimization) of the inspection area are similar to those of the first embodiment, the description is neglected.

(1) Contour Correcting Tool

Figure 7A:
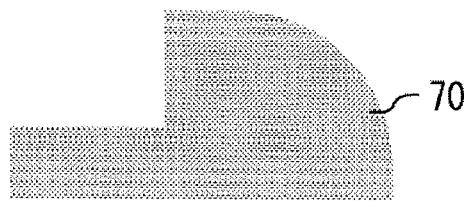
FIGS. 7(a) to 7(e) are views illustrating an operation example of a contour correcting tool.
Figure 7B:
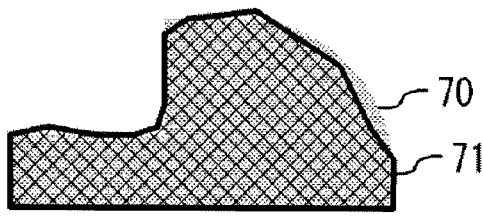

FIGS. 7(a) to 7(e) are views illustrating an operation example of a contour correcting tool. FIG. 7(a) illustrates an image of inspection object (sample) 70, and FIG. 7(b) illustrates an automatic calculation result of inspection area 71. It is assumed that a gap is generated between the contours of inspection object 70 and inspection area 71 as illustrated in FIG. 7(b).

Figure 7C:
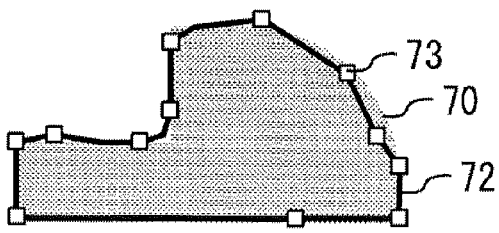
Figure 7D:
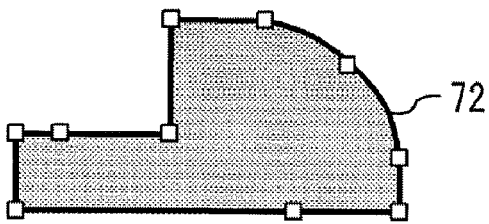
Figure 7E:
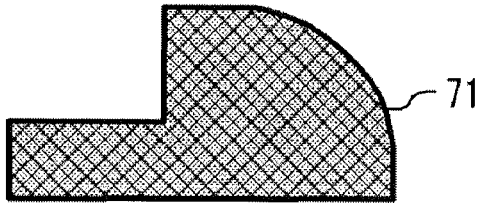

When the user starts up the contour correcting tool, the contour correcting tool approximates the contour of inspection area 71 using path 72 of a Bezier curve or a spline curve, and displays path 72 on the screen together with control points 73 as illustrated in FIG. 7(c). At this point, path 72 and control points 73 are overlaid on the image of inspection object 70. The user performs the correction, the addition, and the deletion of control point 73 using input device 14, which allows the shape of path 72 to be freely corrected. The result corrected by the user is instantaneously reflected in the screen display. Accordingly, the user can easily adjust the shape of path 72 to the contour of inspection area 71 while checking the shape of path 72 on the screen. FIG. 7(d) illustrates post-correction path 72.

When the user issues an instruction to confirm the path after the correction of path 72 is completed by the manipulation, the contour correcting tool converts the area surrounded by path 72 into inspection area 71. Therefore, inspection area 71 having the shape intended by the user is obtained.

(2) Contour Drawing Tool

Figure 8A:
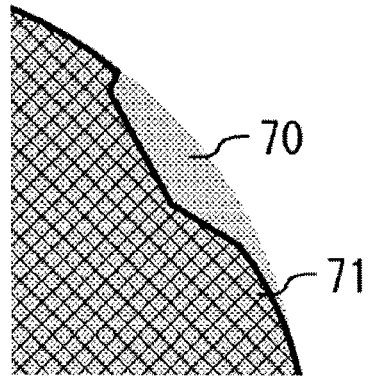
FIGS. 8(a) to 8(c) are views illustrating an operation example of a contour drawing tool.
Figure 8B:
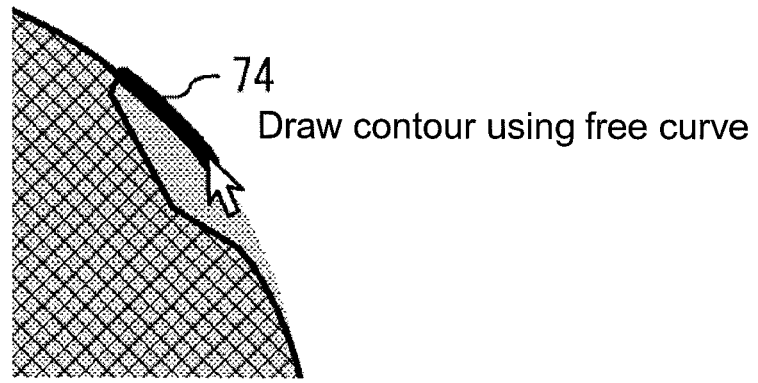
Figure 8C:
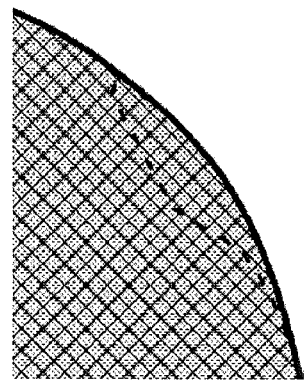

FIGS. 8(a) to 8(c) are views illustrating an operation example of a contour drawing tool. FIG. 8(a) is a partially enlarged view illustrating the image of inspection object 70 and automatically-calculated inspection area 71. It is assumed that a gap is generated between the contours of inspection object 70 and inspection area 71 as illustrated in FIG. 8(a).

When the user starts up the contour drawing tool, the display screen is changed to a contour drawing mode, and free curve 74 can be drawn on the image using input device 14. For example, in the case that a mouse is used as input device 14, a locus of a moving mouse cursor is drawn as free curve 74 from when a button of the mouse is pressed until when the button is released. When the user does not successfully draw free curve 74, the contour drawing mode may be canceled to restart the manipulation from the beginning.

When the user issues the instruction to confirm the contour after the drawing of free curve 74 is completed by the manipulation, the contour drawing tool synthesizes free curve 74 and inspection area 71 such that free curve 74 constitutes a part of the contour of inspection area 71. FIG. 8(c) illustrates post-synthesis inspection area 71. Any technique may be used to synthesize free curve 74 and inspection area 71. For example, smoothing may be performed to smooth a connection portion of free curve 74 and the contour of inspection area 71, or the shape of free curve 74. In the case that an end point of free curve 74 is away from the contour of inspection area 71, free curve 74 and the contour of inspection area 71 may be connected to each other at a nearest neighbor point, or interpolation may be performed such that free curve 74 and the contour of inspection area 71 are smoothly connected to each other. Inspection area 71 having the shape intended by the user is obtained by the above manipulation.

(3) Arc Converting Tool

Figure 9A:
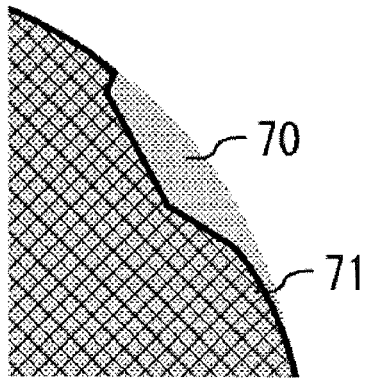
FIGS. 9(a) to 9(c) are views illustrating an operation example of an arc converting tool.
Figure 9A:
Figure 9B:
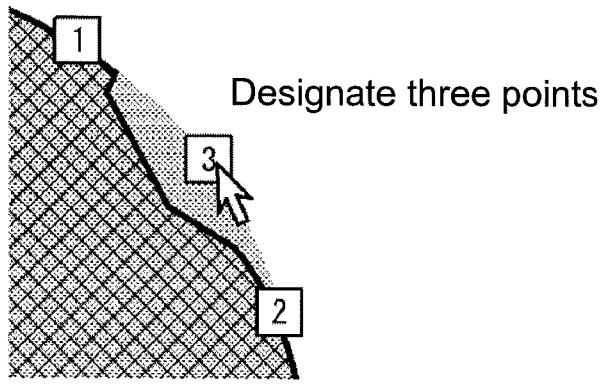
Figure 9B:
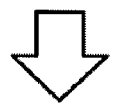
Figure 9C:
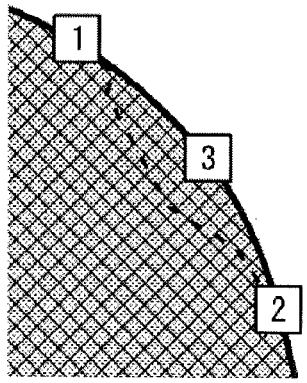

FIGS. 9(a) to 9(c) are views illustrating an operation example of an arc converting tool. FIG. 9(a) is a partially enlarged view illustrating the image of inspection object 70 and automatically-calculated inspection area 71. It is assumed that a gap is generated between the contours of inspection object 70 and inspection area 71 as illustrated in FIG. 9(a).

When the user starts up the arc converting tool, the screen display is changed to an arc input mode, and an arc can be input on the image using input device 14. For example, in the case that the mouse is used as input device 14, the mouse cursor is moved and clicked at three points, namely, two points (1 and 2) on the contour of inspection area 71 and a passing point (3) of the arc as illustrated in FIG. 9(b). Therefore, the arc passing through the point 3 with the points 1 and 2 as the starting and ending points is calculated and overlaid on the image. In the case that the shape of the arc differs from an intended shape, position of each point may be corrected, or the arc input mode may be canceled to restart the manipulation from the beginning. In the second embodiment, the arc is designated by the three points of the arc, namely, the starting point, the ending point, and the passing point. Alternatively, the arc may be input by another designation method.

When the user issues the instruction to confirm the arc after the designation of the arc is completed by the manipulation, the arc converting tool substitutes the contour in an interval between the starting point (1) and the ending point (2) in the contour of inspection area 71 for the arc. At this point, in the case that the starting point (1) or the ending point (2) is away from the contour of inspection area 71, the arc and the contour of inspection area 71 may be connected to each other at the nearest neighbor point, or the interpolation may be performed such that the arc and the contour of inspection area 71 are smoothly connected to each other. The contour in the partial interval of inspection area 71 can easily be shaped into the arc by the above manipulation.

(4) Line Converting Tool

Figure 10A:
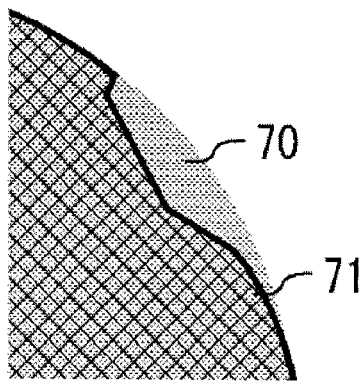
FIGS. 10(a) to 10(c) are views illustrating an operation example of a line converting tool.
Figure 10B:
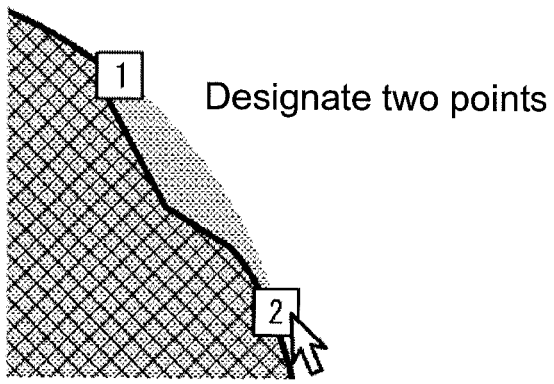
Figure 10C:
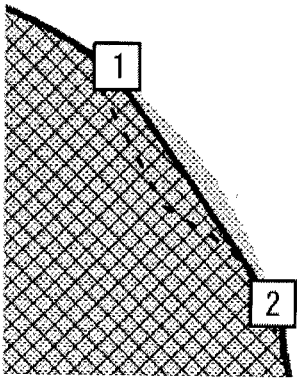

FIGS. 10(a) to 10(c) are views illustrating an operation example of a line converting tool. FIG. 10(a) is a partially enlarged view illustrating the image of inspection object 70 and automatically-calculated inspection area 71. It is assumed that a gap is generated between the contours of inspection object 70 and inspection area 71 as illustrated in FIG. 10(a).

When the user starts up the line converting tool, the screen display is changed to a line input mode, and a line segment can be input on the image using input device 14. For example, in the case that the mouse is used as input device 14, the mouse cursor is moved and clicked at two points (1 and 2) on the contour of inspection area 71 as illustrated in FIG. 10(b). Therefore, the line segment in which the points 1 and 2 are set to the starting and ending points is calculated and overlaid on the image. In the case that the shape of the line segment differs from an intended shape, position of each point may be corrected, or the line input mode may be canceled to restart the manipulation from the beginning. In the second embodiment, the line is designated by the two points, namely, the starting point, and the ending point. Alternatively, the line may be input by another designation method.

When the user issues the instruction to confirm the line after the designation of the line is completed by the manipulation, the line converting tool substitutes the contour in the interval between the starting point (1) and the ending point (2) in the contour of inspection area 71 for the line segment. At this point, in the case that the starting point (1) or the ending point (2) is away from the contour of inspection area 71, the line segment and the contour of inspection area 71 may be connected to each other at the nearest neighbor point, or the interpolation may be performed such that the line segment and the contour of inspection area 71 are smoothly connected to each other. The contour in the partial interval of inspection area 71 can easily be shaped into the line by the above manipulation.

(5) Draw Tool

FIGS. 11(a) to 11(c) are views illustrating an operation example of a draw tool. FIG. 11(a) is a partially enlarged view illustrating the image of inspection object 70 and automatically-calculated inspection area 71. In the draw tool, because inspection area 71 is corrected in units of pixels, a grid of pixels is illustrated in FIGS. 11(a) to 11(c) for the sake of convenience. It is assumed that a gap is generated between the contours of inspection object 70 and inspection area 71 as illustrated in FIG. 11(a), that inspection area 71 is smaller than inspection object 70 in the upper portion of FIG. 11(a), and that inspection area 71 is larger than inspection object 70 in the right of FIG. 11(a).

When the user starts up the draw tool, the screen display is changed to a draw mode, and a pixel to be added to inspection area 71 can be designated on the image using input device 14 or a pixel to be deleted from inspection area 71 can be designated on the image using input device 14. FIG. 11(b) illustrates a state in which pixels are added to the inspection area. For example, in the case that the mouse is used as input device 14, pixels to be added are sequentially selected or the mouse cursor is moved while a predetermined button is pressed, whereby area (pixel group) 75 to be added to inspection area 71 can be designated. On the other hand, FIG. 11(c) illustrates a state in which pixels are deleted from the inspection area. Area (pixel group) 76 to be deleted from inspection area 71 can be designated similarly to the addition. Inspection area 71 having a shape intended by the user is obtained by the above manipulation.

According to the configuration of the second embodiment provided with the function of correcting the shape of the inspection area, a portion hardly automatically extracted by the computing machine can be complemented by the user aid, and therefore an optimal inspection area (that is, the inspection area having the user's desired shape) can simply be obtained in a short time. Although the correcting functions (1) to (5) are described in the second embodiment, the setting tool does not necessarily include all the correcting functions. At least one of the functions may be provided, and according to one or more embodiments of the present invention, the setting tool includes another correcting function. According to one or more embodiments of the present invention, during the correcting work, the user can enlarge/reduce the work screen in FIGS. 7(*a*) to 11(*c*) to proceed efficiently with the work or to easily perform a precise input.

The above embodiments of the present invention are illustrated only by way of example, but the scope of the invention is not limited to the embodiments. For example, although the color information on the image is used in one or more of the embodiments because the color image is considered as the sample image, in the case that a monochrome image is used, brightness information may be used instead of the color information. In addition, although the graph cut algorithm is used in the optimization in one or more of the embodiments, other methods such as a level set algorithm may be used. For other methods, the inspection area can accurately be calculated using the color information (brightness information) and the edge information. In this case, according to one or more embodiments of the present invention, the user can also change the priority between the color information (brightness information) and the edge information.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF SYMBOLS

1 image inspecting device
2 inspection object (chassis component)
10 device body
11 image sensor
12 display device
13 storage device
14 input device
101 inspection processor
102 inspection area extracting unit
103 setting tool
20 hinge portion
21 button portion
30 inspection area
31 inspection area image
50 image window
51 image capturing button
52 foreground designating button
53 background designating button
54 priority adjusting slider
55 confirm button
70 inspection object
71 inspection area
72 path
73 control point
74 free curve

The invention claimed is:

1. An inspection area setting method for setting inspection area-defining information defining an inspection area to an image inspecting device, the image inspecting device being configured to extract a portion constituting the inspection area as an inspection area image from an original image obtained by taking an image of an inspection object, and to inspect the inspection object by analyzing the inspection area image, the inspection area setting method comprising:
   an acquisition step of acquiring a sample image obtained by taking an image of a sample of the inspection object;
   an inspection area searching step of acquiring an optimal solution of the inspection area from a plurality of candidate areas by evaluating both pixel separation and edge overlap with respect to the plurality of candidate areas that are of candidate solutions of the inspection area based on information on color or brightness of each pixel in the sample image and information on an edge comprised in the sample image, the pixel separation being a degree of separation of the color or the brightness between an inside and an outside of each candidate area, the edge overlap being an overlap degree between an contour of each candidate area and the edge in the sample image; and
   a setting step of setting inspection area-defining information defining a position and a shape of the contour of the inspection area obtained in the inspection area searching step to the image inspecting device.

2. The inspection area setting method according to claim 1, further comprising:
   a parameter receiving step of receiving input of a parameter from a user,
   wherein, every time the input of the parameter is received from the user in the parameter receiving step, the inspection area searching step is performed with the input parameter as a constraint condition to recalculate the optimal solution of the inspection area, and displays the recalculated inspection area on a display device.

3. The inspection area setting method according to claim 2, wherein, the parameter receiving step comprises receiving a balance parameter inputted the user as one kind of the parameter in order to adjust a balance between the pixel separation and the edge overlap, and
   wherein, in the inspection area searching step, weight are adjusted in evaluating the pixel separation and the edge overlap according to the balance parameter input from the user.

4. The inspection area setting method according to claim 2, wherein a value obtained by evaluating a likelihood of a foreground of the color or the brightness of each pixel inside the candidate area with respect to representative color or representative brightness of the foreground, a value obtained by evaluating a likelihood of a background of the color or the brightness of each pixel outside the candidate area with respect to representative color or representative brightness of the background, or a value obtained by synthesizing both the values is used as the pixel separation in the inspection area searching step.

5. The inspection area setting method according to claim 4, wherein, in the inspection area searching step, the weight is adjusted in evaluating the pixel separation and the edge overlap such that the weight of the pixel separation increases with increasing difference between the representative color or the representative brightness of the foreground and the representative color or the representative brightness of the background, and such that the weight of the edge overlap increases with decreasing difference.

6. The inspection area setting method according to claim 4, wherein parameter receiving step comprises receiving the representative color or the representative brightness of the foreground, the background, or the both inputted by the user as one kind of the parameter.

7. The inspection area setting method according to claim 6, wherein parameter receiving step comprises:
   Displaying the sample image on the display device,
   Receiving a portion to be the foreground or the background on the displayed sample image designated by the user, and
   Acquiring the color or the brightness of the designated portion as the representative color or the representative brightness.

8. The inspection area setting method according to claim 2, wherein the parameter receiving step comprises receiving shape information expressing a feature related to the shape of the inspection area inputted by the user as one kind of the parameter, and
wherein, in the inspection area searching step, the optimal solution of the inspection area is obtained such that a degree of similarity between the shape of the inspection area and a shape expressed by the shape information increases in addition to the pixel separation and the edge overlap.

9. The inspection area setting method according to claim 2, wherein the parameter receiving step comprises receiving size information expressing a feature related to a size of the inspection area inputted by the user as one kind of the parameter, and
wherein, in the inspection area searching step, the optimal solution of the inspection area is obtained such that a degree of similarity between the size of the inspection area and a size expressed by the shape information increases in addition to the pixel separation and the edge overlap.

10. The inspection area setting method according to claim 2,
wherein the parameter receiving step comprises receiving position information expressing a feature related to a position in the image of the inspection area inputted by the user as one kind of the parameter, and
wherein, in the inspection area searching step, the optimal solution of the inspection area is obtained such that a degree of similarity between the position in the image of the inspection area and a position expressed by the position information increases in addition to the pixel separation and the edge overlap.

11. The inspection area setting method according to claim 2,
wherein, in the parameter receiving step comprises receiving texture information expressing a feature related to a texture of the image in the inspection area inputted by the user as one kind of the parameter, and
wherein, in the inspection area searching step, the optimal solution of the inspection area is obtained such that a degree of similarity between the texture of the image in the inspection area and a texture expressed by the texture information increases in addition to the pixel separation and the edge overlap.

12. The inspection area setting method according to claim 1, further comprising:
   An inspection area correcting step of displaying the inspection area obtained in the inspection area searching step on the display device, and correcting the shape of the inspection area according to a correction instruction input from the user.

13. The inspection area setting method according to claim 12,
wherein, in the inspection area correcting step, a whole or a part of the contour of the inspection area is approximated using a path of a Bezier curve or a spline curve and the user corrects the path.

14. The inspection area setting method according to claim 12,
Wherein the inspection area correcting step comprises:
   Receiving a free curve drawn by the user, and
   Synthesizing the free curve and the inspection area such that the free curve constitutes a part of the contour of the inspection area.

15. The inspection area setting method according to claim 12,
Wherein the inspection area correcting step comprises:
   Receiving an interval of a part of the contour of the inspection area designated by the user, and
   Replacing the contour of the designated interval with a straight line or an arc.

16. The inspection area setting method according to claim 12,
Wherein the pixel designated by the user is added to the inspection area or excluded from the inspection area in the inspection area correcting step.

17. A computer program stored on a non-transitory computer-readable medium that causes a computer to perform an inspection area setting method for setting inspection area-defining information defining an inspection area to an image inspecting device, the image inspecting device being configured to extract a portion constituting the inspection area as an inspection area image from an original image obtained by taking an image of an inspection object, and to inspect the inspection object by analyzing the inspection area image, the inspection area setting method comprising:
   An acquisition step of acquiring a sample image obtained by taking an image of a sample of the inspection object;
   an inspection area searching step of acquiring an optimal solution of the inspection area from a plurality of candidate areas by evaluating both pixel separation and edge overlap with respect to the plurality of candidate areas that are of candidate solutions of the inspection area based on information on color or brightness of each pixel in the sample image and information on an edge comprised in the sample image, the pixel separation being a degree of separation of the color or the brightness between an inside and an outside of each candidate area, the edge overlap being an overlap degree between an contour of each candidate area and the edge in the sample image; and
   A setting step of setting inspection area-defining information defining a position and a shape of the contour of the inspection area obtained in the inspection area searching step to the image inspecting device.

18. An inspection area setting device configured to set inspection area-defining information defining an inspection area to an image inspecting device, the image inspecting device being configured to extract a portion constituting the inspection area as an inspection area image from an original image obtained by taking an image of an inspection object, and to inspect the inspection object by analyzing the inspection area image, the inspection area setting device comprising:

An image sensor that acquires a sample image by taking an image of a sample of the inspection object; and A processor that obtains an optimal solution of the inspection area from a plurality of candidate areas by evaluating both pixel separation and edge overlap with respect to the plurality of candidate areas that are of candidate solutions of the inspection area based on information on color or brightness of each pixel in the sample image and information on an edge comprised in the sample image, the pixel separation being a degree of separation of the color or the brightness between an inside and an outside of each candidate area, the edge overlap being an overlap degree between an contour of each candidate area and the edge in the sample image, and sets inspection area-defining information defining a position and a shape of the contour of the obtained inspection area to the image inspecting device.

* * * * *